US010413476B2

United States Patent
Giarracco et al.

(10) Patent No.: US 10,413,476 B2
(45) Date of Patent: Sep. 17, 2019

(54) SYSTEM AND METHOD FOR CARDIOPULMONARY RESUSCITATION

(71) Applicant: COVIDIEN LP, Mansfield, MA (US)

(72) Inventors: David J. Giarracco, Boulder, CO (US); Paul S. Addison, Edinburgh (GB); James N. Watson, Edinburgh (GB); Daniel Lisogurski, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 810 days.

(21) Appl. No.: 15/000,770

(22) Filed: Jan. 19, 2016

(65) Prior Publication Data

US 2016/0206504 A1  Jul. 21, 2016

Related U.S. Application Data

(60) Provisional application No. 62/105,305, filed on Jan. 20, 2015.

(51) Int. Cl.
*A61H 31/00* (2006.01)
*A61B 5/00* (2006.01)
(Continued)

(52) U.S. Cl.
CPC ......... *A61H 31/005* (2013.01); *A61B 5/0261* (2013.01); *A61B 5/14551* (2013.01);
(Continued)

(58) Field of Classification Search
CPC ................ A61H 31/005; A61H 31/007; A61H 2201/5097; A61H 2201/5015;
(Continued)

(56) References Cited

U.S. PATENT DOCUMENTS 4,960,126 A  10/1990  Conlon et al.
5,078,136 A  1/1992  Stone et al.
(Continued)

FOREIGN PATENT DOCUMENTS

CN  103860180 A  6/2014
EP  1491175 A1  12/2004
(Continued)

OTHER PUBLICATIONS

Addison, P., et al.; "Evaluating Arrhythmias in ECG Signals Using Wavelet Transforms," IEEE Engineering in Medicine and Biology Sep./Oct. 2000, 0739-5175, pp. 104-109.
(Continued)

*Primary Examiner* — Quang D Thanh
(74) *Attorney, Agent, or Firm* — Cantor Colburn LLP (57) ABSTRACT

A medical monitoring system includes an oximetry sensor having a light emitter positioned to emit light into a patient and a photodetector positioned to generate a plethysmography signal. The system includes a monitor having a processor configured to receive the plethysmography signal from the oximetry sensor and to identify a non-cardiac pulse based on a first pulse shape metric, the non-cardiac pulse being generated by the administration of cardiopulmonary resuscitation (CPR) to the patient. The processor is also configured to measure an oxygen saturation of the patient from the identified non-cardiac pulse and to output the measured oxygen saturation to a visual display.

18 Claims, 6 Drawing Sheets

(51) Int. Cl.
  *A61B 5/026* (2006.01)
  *A61B 5/1455* (2006.01)
  *A61B 5/024* (2006.01)
  *A61B 5/11* (2006.01)

(52) U.S. Cl.
  CPC ......... *A61B 5/7235* (2013.01); *A61H 31/007* (2013.01); *A61B 5/02416* (2013.01); *A61B 5/11* (2013.01); *A61H 2201/5015* (2013.01); *A61H 2201/5043* (2013.01); *A61H 2201/5084* (2013.01); *A61H 2201/5089* (2013.01); *A61H 2201/5092* (2013.01); *A61H 2201/5097* (2013.01); *A61H 2230/00* (2013.01); *A61H 2230/208* (2013.01)

(58) Field of Classification Search
  CPC .......... A61H 2230/00; A61H 2230/208; A61H 2201/5043; A61H 2201/5092; A61H 2201/5089; A61H 2201/5084; A61B 5/7235; A61B 5/14551; A61B 5/0261; A61B 5/11; A61B 5/02416
  See application file for complete search history.

(56) References Cited

U.S. PATENT DOCUMENTS

| | | |
|---|---|---|
| 5,099,841 A | 3/1992 | Heinonen et al. |
| 5,662,105 A | 9/1997 | Tien |
| 5,853,364 A | 12/1998 | Baker, Jr. et al. |
| 6,083,172 A | 7/2000 | Baker, Jr. et al. |
| 6,398,727 B1 | 6/2002 | Bui et al. |
| 6,411,833 B1 | 6/2002 | Baker, Jr. et al. |
| 6,574,491 B2 | 6/2003 | Elghazzawi |
| 6,579,242 B2 | 6/2003 | Bui et al. |
| 6,830,549 B2 | 12/2004 | Bui et al. |
| 7,006,865 B1 | 2/2006 | Cohen et al. |
| 7,112,175 B2 | 9/2006 | Gopinathan et al. |
| 7,171,269 B1 | 1/2007 | Addison et al. |
| 7,222,054 B2 | 5/2007 | Geva |
| 7,373,194 B2 | 5/2008 | Weber et al. |
| 7,435,222 B2 | 10/2008 | Gopinathan et al. |
| 7,569,018 B1 | 8/2009 | Geddes et al. |
| 7,976,472 B2 | 7/2011 | Kiani |
| 8,100,834 B2 | 1/2012 | Shuler |
| 8,190,223 B2 | 5/2012 | Al-Ali et al. |
| 8,224,411 B2 | 7/2012 | Al-Ali et al. |
| 8,983,588 B2 | 3/2015 | Addison et al. |
| 9,155,493 B2 | 10/2015 | Addison et al. |
| 2003/0139656 A1 | 7/2003 | Kiani et al. |
| 2004/0064020 A1 | 4/2004 | Diab et al. |
| 2004/0267324 A1 | 12/2004 | Geheb et al. |
| 2005/0267346 A1 | 12/2005 | Faber et al. |
| 2007/0000531 A1 | 1/2007 | Russo |
| 2007/0270665 A1 | 11/2007 | Yang et al. |
| 2008/0097176 A1 | 4/2008 | Music et al. |
| 2008/0097177 A1 | 4/2008 | Music et al. |
| 2008/0171311 A1 | 7/2008 | Corey et al. |
| 2008/0228045 A1 | 9/2008 | Gao et al. |
| 2010/0168605 A1 | 7/2010 | Aarts |
| 2010/0331715 A1 | 12/2010 | Addison |
| 2011/0270114 A1 | 11/2011 | Addison et al. |
| 2012/0016179 A1* | 1/2012 | Paradis ................ A61H 9/0078 600/17 |
| 2012/0101349 A1 | 4/2012 | DelloStritto et al. |
| 2012/0220844 A1 | 8/2012 | Baker, Jr. |
| 2012/0232365 A1 | 9/2012 | Ukawa |
| 2013/0225952 A1 | 8/2013 | Lin et al. |
| 2013/0338724 A1* | 12/2013 | Joo ...................... A61N 1/3987 607/3 |
| 2014/0073875 A1 | 3/2014 | Pirow et al. |
| 2015/0105636 A1 | 4/2015 | Hayman et al. |
| 2015/0105637 A1* | 4/2015 | Yu ...................... A61B 5/02416 600/324 |
| 2015/0164339 A1* | 6/2015 | Xu ........................ A61B 5/024 600/324 |

FOREIGN PATENT DOCUMENTS

| | | |
|---|---|---|
| EP | 2198823 A1 | 6/2010 |
| EP | 2502560 A1 | 9/2012 |
| EP | 2700357 A1 | 2/2014 |
| WO | 00/38569 A1 | 7/2000 |
| WO | 2004073787 A2 | 9/2004 |
| WO | WO-2006009830 A2 | 1/2006 |
| WO | WO-2006039752 A1 | 4/2006 |
| WO | 2010/096396 A1 | 8/2010 |

OTHER PUBLICATIONS

Addison, P.S., et al.; "Finding Coordinated Atrial Activity During Ventricular Fibrillation Using Wavelet Decomposition"; IEEE Engineering in Medicine and Biology 2002, vol. 21, pp. 58-65.

Watson, J.N. et al.; "Wavelet Transform-based Prediction of the Likelihood of Successful Defibrillation for Patients Exhibiting Ventricular Fibrillation"; Measurement Science and Technology 2005, vol. 16, L1-L6.

Addison, P.S.; "Wavelet Transforms and the ECG: A Review"; Physiological Measurement 2005, vol. 26, pp. R155-199.

Barnum, P.T., et al.; "Novel Pulse Oximetry Technology Capable of Reliable Bradycardia Monitoring in the Neonate," Respiratory Care, vol. 42, No. 1, p. 1072 (Nov. 1997).

Box, M.S., et al.; "Shock Outcome Prediction Before and After CPR: A Comparative Study of Manual and Automated Active Compression—Decompression CPR"; Resuscitation 2008, vol. 78, pp. 265-278.

Chen, Liangyou, et al.; "IS respiration-induced variation in the photoplethysmogram associated with major hypovolemia in patients with actue tramatic injuries," SHOCK, vol. 34, No. 5, pp. 455-460 (2010).

East, Christine E., et al.; "Fetal Oxygen Saturation and Uterine Contractions During Labor," American Journal of Perinatology, vol. 15, No. 6, pp. 345-349 (Jun. 1998).

Endoh, H., et al.; "Prompt Prediction of Successful Defibrillation From 1-s Ventricular Fibrillation Waveform in Patients with Out-of-hospital Sudden Cardiac Arrest"; T. Journal of Anesthesia 2011, vol. 25(1), pp. 34-41.

Gesquiere, Michael J., et al., "Impact of withdrawal of 450 ML of blook on respiration-induced oscillations of the ear plethysmographic waveform," Journal of Clinical Monitoring and Computing (2007) 21:277-282.

Gundersen, K., et al.; "Identifying Approaches to Improve the Accuracy of Shock Outcome Prediction for Out-of-Hospital Cardiac Arrest"; Resuscitation 2008, vol. 76, pp. 279-284.

Gundersen, K.,; "Using ECG-Analysis to Quantify the Effect of Increasing Pre-Shock Pauses in Chest Compressions on the Probability of ROSC"; Resuscitation 2008, pp. S18-S19.

Hall, M., et al.; "Myocardial Substrate in Secondary Ventricular Fibrillation: Insights from Quantitative Waveform Measures"; Secondary VF and Waveform Measures 2011, vol. 15(3), pp. 388-393.

He, M., et al.; "Prediction of Defibrillation Outcome by Ventricular Fibrillation Waveform Analysis: A Clinical Review;" J Clinic Experiment Cardiol 2013, S10, pp. 1-8.

Johansson, A.; "Neural network for photoplethysmographic respiratory rate monitoring," Medical & Biological Engineering & Computing, vol. 41, pp. 242-248 (2003).

Johnston, W.S., et al.; "Extracting Breathing Rate Infromation from a Wearable Reflectance Pulse Oximeter Sensor," Proceedings of the 26th Annual International conference of the IEEE EMBS, San Francisco, California; Sep. 1-5, 2004; pp. 5388-5391.

Matthews, Nora S. et al.; "An evaluation of pulse oximeters in dogs, cats and horses," Veterinary Anaesthesia and Analgesia, vol. 30, pp. 3-14 (2003).

McGrath, S.P., et al.; "Pulse oximeter plethysmographic waveform changes in awake, spontaneously breathing, hypovolemic volunteers," Anesth. Analg. vol. 112 No. 2, pp. 368-374 (2010).

Nakagawa, Y., et al.; "Amplitude Spectral Area: Predicting the Success of Electric Shock Delivered by Defibrillators with Different Waveforms"; Tokai J Exp Clin Med. 2013, vol. 38(2), pp. 71-76.

(56) References Cited

OTHER PUBLICATIONS

Nilsson, Lena, et al.; "Monitoring of Respiratory Rate in Postoperative Care Using a New Photoplethysmographic Technique," Journal of Clinical Monitoring and Computing, vol. 16, pp. 309-315 (2000).
Pickett, John, et al.; "Pulse Oximetry and PPG Measurements in Plastic Surgery," Proceedings—19th International Conference—IEEE/EMBS, Chicago, Illinois, Oct. 30-Nov. 2, 1997, pp. 2330-2332.
Relente, A.R., et al.; "Characterization and Adaptive Filtering of Motion Artifacts in Pulse Oximetry using Accelerometers," Proceedings of the Second joint EMBS/BMES Conference, Houston, Texas, Oct. 23-26, 2002; pp. 1769-1770.
Seelbach-Gobel, Birgit, et al.; "The prediction of fetal acidosis by means of intrapartum fetal pulse oximetry," Am J. Obstet. Gynecol., vol. 180, No. 1, Part 1, pp. 73-81 (1999).
Shamir, M., et al.; "Pulse oximetry plethysmographic waveform during changes in blood volume," British Journal of Anaesthesia 82(2): 178-81 (1999).
Sherman, L., et al.; "Beta-Blockade Causes a Reduction in the Frequency Spectrum of VF but Improves Resuscitation Outcome: A Potential Limitation of Quantitative Waveform Measures"; Resuscitation 2012, vol. 83, pp. 511-516.
Sherman, L., et al.; "IThe Comparison of 6 Quantitative Waveform Measures in Measuring the Deterioration of Untreated VF"; Journal of Electrocardiology 2011, vol. 44, p. e12.
Sipgulis, Janis, et al.; "Optical multi-channel sensing of skin blood pulsations," Optical Sensing, Proceedings of SPIE, vol. 5459, pp. 46-53 (2004).
Stiles, M.K., et al.; "Wavelet Based Analysis of Heart-Rate-Dependent ECG Features"; Annals of Noninvasive Electrocardiology 2004, vol. 9(4), pp. 316-322.
Watson, J.N., et al.; "A Novel Wavelet Transform Based Analysis Reveals Hidden Structure in Ventricular Fibrillation"; Resuscitation 2000, vol. 43(2), pp. 121-127.
Watson, J.N., et al.; "Angular Velocity: a new method to improve prediction of ventricular fibrillation duration;" Resuscitation Letter—Published Paper 2004, vol. 62 pp. 124-125.
Watson, J.N., et al.; "Improved Prediction of Defibrillation Success for Out-of-Hospital VF Cardiac Arrest Using Wavelet Transform Methods"; Resuscitation 2004, vol. 63(3), pp. 269-275.
Watson, J.N., et al.; "Practical Issues in the Evaluation of Methods for the Prediction of Shock Outcome Success in Out-of-hospital Sudden Cardiac Arrest Patients"; Resuscitation 2006, vol. 68, pp. 51-59.
Watson, J.N., et al.; "Wavelet Transform Analysis Predicts Outcome of DC Cardioversion for Atrial Fibrillation Patients"; Computers in Biology and Medicine 2007, vol. 37, pp. 517-523.
Wik, L., et al.; "Delaying Defibrillation to Give Basic Cardiopulmonary Resuscitation to Patients With Out-of-Hospital Ventricular Fibrillation;" American Medical Association 2003, vol. 289, No. 11, pp. 1389-1395.
Wu, Dongmei, et al.; "Na*/H* Exchange inhibition delays the onset of hypovolemic circulatory shock in pigs," SHOCK, vol. 29, No. 4, pp. 519-525 (2008).
Yoon, Gilwon, et al.; "Multiple diagnosis based on Photoplethysmography: hematocrit, SpO2, pulse and respiration," Optics in Health Care and Biomedical optics: Diagnostics and Treatment; Proceedings of the SPIE, vol. 4916; pp. 185-188 (2002).
Ralph W.C.G.R. Wijshoff et al.; "Photoplethysmography-Based Algorithm for Detection of Cardiogenic Output during Cardiopulmonary Resuscitation," IEEE Transactions on Biomedical Engineering, vol. 62, No. 3, Nov. 13, 2014; pp. 909-921.
Ralph W.C.G.R. Wijshoff et al.; "Detection of a spontaneous pulse in phtoplethysmograms during automated cardiopulmonary resuscitation in a porcine model," Resuscitation, vol. 84, No. 11, Nov. 1, 2013; pp. 1625-1632.
International Search Report and Written Opinion for PCT Application No. PCT/US2016/014069 dated Apr. 26, 2016, 20 pgs.

\* cited by examiner

SYSTEM AND METHOD FOR CARDIOPULMONARY RESUSCITATION

CROSS-REFERENCE TO RELATED APPLICATION

This application claims priority to and the benefit of Provisional Application No. 62/105,305, entitled "SYSTEM AND METHOD FOR CARDIOPULMONARY RESUSCITATION," filed Jan. 20, 2015, which is incorporated by reference herein in its entirety.

BACKGROUND

The present disclosure relates generally to cardiopulmonary resuscitation and, more particularly, to systems and methods for assisting a person in performing resuscitation.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In many medical emergencies, a person's heart may stop pumping on its own. The person may need emergency resuscitation, such as cardiopulmonary resuscitation (CPR) to sustain the life of the person by manually maintaining intact brain function. Typically, CPR involves manually pumping the chest (i.e., chest compressions) to force blood through the cardiovascular system to organs such as the brain. CPR also involves occasionally blowing oxygenated air (i.e., administered breaths or artificial respiration) into the lungs of the person so that oxygen may be absorbed into the bloodstream. However, the person administering the CPR, whether a trained emergency responder or a person with little training or experience in administering CPR, has little to no feedback as to the effectiveness of the CPR (e.g., quality of chest compressions or applied breaths) being administered. Consequently, the CPR may not be administered as effectively as possible.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. Also, as used herein, the term "over" or "above" refers to a component location on a sensor that is closer to patient tissue when the sensor is applied to the patient.

The present embodiments relate generally to emergency response kits (i.e., emergency response components described below provided or sold as a single unit for use in an emergency response) that may include a sensor and/or monitor to monitor one or more physiological characteristics (e.g., oxygen saturation ($SpO_2$) of a patient (i.e., person receiving emergency resuscitation, such as CPR). Examples include pulse oximetry sensors and monitors. The pulse oximetry sensors described herein may incorporate one or more emitters and one or more detectors for emitting light into a patient at one or more wavelengths, and detecting a signal representative of reflected or transmitted light received from the patient. This acquired signal may be used to determine the level of blood oxygen saturation in an artery of the patient. This signal may be referred to as a photoplethysmography signal or photoplethysmograph. This signal typically reflects cardiac pulses in the patient's blood due to contractions of the heart. During CPR, this signal may include non-cardiac pulses—pulses due to the administration of chest compressions during CPR, rather than to contraction of the patient's heart. As discussed in more detail below, in certain embodiments of the present disclosure, a sensor may be configured to monitor regional regional oxygen saturation (rSO$_2$) of a patient.

While guidelines related to performance of CPR exist (e.g., chest compression rate, depth and frequency of breathing, or the like), the presently disclosed systems and methods may provide improved patient outcomes by facilitating optimization of CPR for the anatomy and physiology of the patient and adapting the CPR over time as the patient's condition changes. In particular, characteristics or features of the signal acquired by the sensor from the patient may provide useful feedback related to the administration of the CPR. For example, as discussed in more detail below, these characteristics or features may include characteristics of non-cardiac pulses, such as an amplitude of the pulse. The amplitude may refer to an absolute amplitude or a relative measure, such as an area under the curve of a non-cardiac pulse. The amplitude of the non-cardiac pulses may generally relate to the quality of administered chest compressions (e.g., appropriate location of chest compressions and/or strength of chest compressions). As discussed below, the amplitude may be compared to similar features from previous non-cardiac pulses and/or to cardiac pulses obtained during normal perfusion in the same patient (e.g., obtained prior to cardiac arrest) and/or to empirical data. An algorithm for analyzing the amplitude of the non-cardiac pulses may take into account changes in body position, which may affect the pulse, for example by detecting from a position sensor (e.g., an accelerometer) that the patient moved from a standing position to a supine position, for example. In some embodiments, the amplitude of the non-cardiac pulses may be normalized by the baseline of the signal. In addition, an SpO$_2$ value derived from the signal may be used to provide useful feedback related to the administration of the CPR. For example, the SpO$_2$ value may relate to the quality (e.g., effectiveness with regards to volume or frequency) of the breaths (i.e., artificial respiration) administered during the CPR. As discussed in more detail below, an rSO$_2$ value may additionally or alternatively be used to provide feedback related to the administration of the CPR.

To facilitate accurate monitoring of signal characteristics (e.g., the amplitude of the non-cardiac pulses) and/or SpO$_2$ during CPR, the sensor and/or the monitor disclosed herein may be configured to apply a pulse identification or qualification algorithm to identify and/or qualify modulations in the signal due to CPR (e.g., non-cardiac pulses). Such non-cardiac pulses may be qualified based on any of a variety of metrics (e.g., parameters), such as one or more pulse shape metrics (e.g., an amplitude variability, a center of area, a rotational moment, a mean, a median, a standard deviation, kurtosis, a pulse wave area, rise time, fall time, a mean path ratio, presence or absence of a dicrotic notch, a natural frequency, a damping factor, a skew, a derivative skew, or any combination thereof). In some embodiments, an amplitude may be used as a pulse shape metric to qualify non-cardiac pulses and/or the amplitude may be analyzed to evaluate the CPR. The metrics may be indicative of a feature of the non-cardiac pulse and may be compared with pulse qualification criteria to qualify or to disqualify the pulse as a non-cardiac pulse due to CPR. In some embodiments, the pulse qualification criteria may be adjusted based on whether the CPR is being performed or assisted by an automated CPR device or being performed manually by a person. Such qualification may differentiate the non-cardiac pulses due to CPR from noise (e.g., due to motion, ambient light, or the like), thereby enabling accurate determination of the signal characteristics (e.g., the amplitude of the non-cardiac pulses) and/or SpO$_2$ during CPR.

In some embodiments, the sensor and/or the monitor may compare a particular signal characteristic (e.g., amplitude of the non-CPR pulses) to a threshold or a range (e.g., optimal range) and/or may compare the SpO$_2$ value to a threshold or a range to determine whether a component of the CPR needs to be altered (e.g., faster/slower or shallower/deeper chest compressions and/or more or fewer breaths). The optimal ranges and/or thresholds may be based on characteristics of the patient (e.g., infant vs. adult, size of patient, age, etc.). The feedback (e.g., efficacy, recommendations, appropriate adjustments, or the like) regarding the administration of the CPR may be communicated from the sensor and/or the monitor to the person administering the CPR (e.g., via a speaker and/or a display). In certain embodiments, the sensor may communicate via a wired connection (e.g., cable) or wirelessly with the monitor. Alternatively, the sensor may include some or all of the hardware (e.g., speaker, display, memory, processing device, etc.) and/or software to analyze the characteristics of the signals and to communicate any feedback to the person administering the CPR. It should be noted that CPR as described herein includes the components of administering chest compressions and artificial respiration. However, the techniques and systems described herein may also be utilized in conjunction with any type of CPR (e.g., CPR administered without artificial respiration). In addition, additional emergency response techniques (e.g., defibrillation or cardiac pacing) may be utilized with CPR.

Additionally, as discussed in more detail below, certain embodiments of the sensor and/or monitor (e.g., a controller of the sensor and/or monitor) may be configured to identify when the patient experiences a return of spontaneous circulation (ROSC) (e.g., return to sustained perfusing cardiac function after cardiac arrest). The sensor and/or the monitor may be configured to scan and/or to analyze the signal obtained from the sensor to identify the ROSC based on any of a variety of metrics (e.g., parameters), such as one or more pulse shape metrics (e.g., a center of area, a rotational moment, a mean, a median, a standard deviation, kurtosis, a pulse wave area, rise time, fall time, a mean path ratio, presence or absence of a dicrotic notch, a natural frequency, a damping factor, a skew, a derivative skew, or any combination thereof) to identify cardiac pulses in the signal. Additionally or alternatively, the sensor and/or the monitor may be configured to identify the ROSC based on a correlation, or a lack of a correlation, between pulses of the signal and a time of application of chest compressions. The sensor and/or the monitor may be configured to provide feedback related to the ROSC. For example, the sensor and/or the monitor may communicate that the ROSC has occurred and/or provide instructions to stop the administration of CPR.

Figure 1:
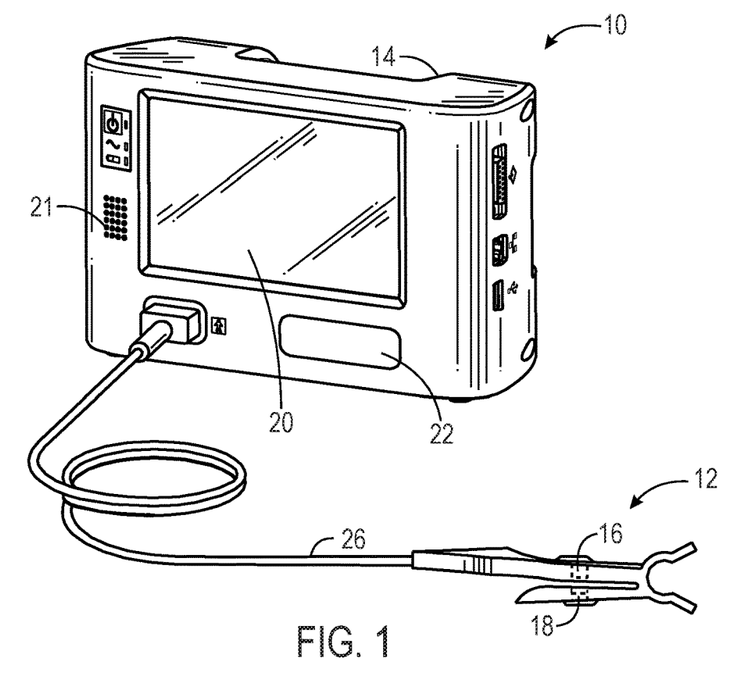
FIG. 1 is a perspective view of an embodiment of a medical monitoring system configured to monitor oxygen saturation, in accordance with an aspect of the present disclosure.

With the foregoing in mind, FIG. 1 depicts an embodiment of a patient monitoring system 10 that includes a patient monitor 14 that may be used in conjunction with a medical sensor 12. Although the depicted embodiments relate to sensors for use on a patient's finger, it should be understood that, in certain embodiments, the sensor 12 as provided herein may be adapted for use at other tissue locations. In addition, the system 10 may be configured to obtain a variety of medical measurements with a suitable medical sensor.

The sensor 12 is communicatively coupled to the patient monitor 14. The sensor 12 may be reusable, entirely disposable, or include disposable portions. Although only one sensor 12 is shown coupled to the monitor 14 in FIG. 1, in other embodiments, two, three, four, or more sensors 12 may be coupled to the monitor 14. For example, two sensors 12 may be used for simultaneously monitoring blood oxygen saturation at two different body locations of the patient. As shown in FIG. 1, the sensor 12 includes an emitter 16 and a detector 18. The sensor 12 is coupled to the monitor 14 via a cable 26. The cable 26 may interface directly with the sensor 12 and may include a plurality of conductors (e.g., wires). Alternatively, the sensor may communicate with the monitor wirelessly.

The monitor 14 includes a monitor display 20 configured to display information regarding the physiological parameters monitored by the sensor 12, information related to the signal obtained by the sensor 12, information about the system, and/or alarm indications, for example. In addition, the monitor display 20 may be configured to provide feedback or communicate information related to the CPR being administered to the patient. As discussed in more detail below, the monitor display 20 may provide information related to chest compressions (e.g., "alter compressions," "change location of compressions," "compression too light," "compression too hard," "slow down compressions," "speed up compressions," etc.) and/or artificial respiration ("give more breaths" or "give fewer breaths"). This information may relate to altering chest compressions and/or administered breaths, changing a location of the chest compressions, changing the amount of force applied during the chest compressions (e.g., too light, too hard, etc.), and/or the effectiveness of the administered breaths (e.g., an amount, frequency, etc.). The information may be displayed via text, images, and/or color-coded indicators.

The monitor 14 may also include a speaker 21 to provide feedback or communicate information related to the CPR being administered to the patient. For example, the speaker 21 may communicate audible instructions (e.g., "change location of compressions," "compression too light," "compression too hard," "slow down compressions," "speed up compressions," etc.). In addition, the speaker 21 may emit a sound (e.g., beep) to reflect a detected pulse (e.g., a qualified non-cardiac pulse). In some embodiments, a pitch, tone, or other characteristic of the sound may be varied to indicate chest compressions are being administered too fast, too slow, or at a correct rate. The monitor 14 may include various input components 22 (e.g., input), such as knobs, switches, keys and keypads, buttons, touchscreen, etc., to provide for operation and configuration of the monitor 14. The input components 22 may enable the inputting and/or adjusting of patient characteristics (e.g., patient age, size, condition, etc.), inputting that the sensor 12 has been applied to the patient, inputting a beginning and/or end of the administration of CPR to the patient (e.g., initiation of "CPR mode"), and/or inputting and/or adjusting ranges, values, and/or thresholds related to determining the effectiveness of the administered CPR (e.g., optimal amplitude of non-cardiac pulse range, optimal pulse frequency range, optimal pulse rate range, optimal $SpO_2$ value, threshold, or range). In certain embodiments, the sensor 12 may include input components for inputting and/or adjusting this information. In certain embodiments, patient characteristics may be determined based on a type of sensor 12 utilized (e.g., an age of the patient may be determined based on whether the sensor 12 is intended for use with neonatal, pediatric, infant, or adult patients.)

As discussed in more detail below, the monitor 14 also includes a processor that may be used to execute code stored in memory, such as code for implementing various monitoring functionalities. As discussed below, for example, the monitor 14 may be configured to process signals generated by the detector 18 to qualify non-cardiac pulses due to the administration of CPR, identify signal characteristics (e.g., the amplitude of the non-cardiac pulses), compare signal characteristics to a threshold or range, provide feedback (e.g., instructions or information) based on the comparison, estimate the $SpO_2$, and/or provide instructions or information based on the estimated $SpO_2$. In addition, the monitor 14 may be configured to relate the $SpO_2$ value to the artificial respiration provided during the CPR. Further, the monitor 14 may be configured to analyze the signals generated by the detector 18 to relate signal characteristics (e.g., the amplitude of the non-cardiac pulses) to chest compressions provided during the CPR. As discussed in more detail below, in some embodiments, the monitor 14 may be configured to identify a return to spontaneous circulation (ROSC). In some embodiments, the processor and memory may be located in the sensor 12 itself, rather than a separate monitor.

In certain embodiments, the sensor 12 may be a wireless sensor 12. Accordingly, the wireless sensor 12 may establish a wireless communication with the patient monitor 14 and/or network using any suitable wireless standard. By way of example, the wireless module may be capable of communicating using one or more of the ZigBee standard, WirelessHART standard, Bluetooth standard, IEEE 802.11x standards, or MiWi standard. In certain embodiments, sensor 12 may be entirely or partially reusable and integrated with the monitor 14 in a single unit having its own display and utilizing no cable 26. The integrated monitor could be a standalone unit, configured to be strapped to the patient and in direct view of the operator. Such embodiment would present the advantages of greater mobility and reduced number of parts. Alternatively, the sensor 12 may include a short cable 26 to a wireless module that transmits the acquired signal and any other sensor information wirelessly to a remote monitor 14.

Figure 2:
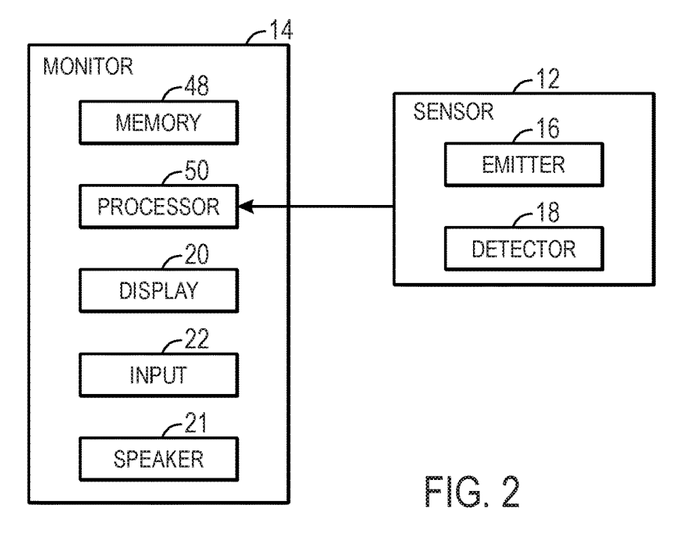
FIG. 2 is a block diagram of the medical monitoring system of FIG. 1, in accordance with an aspect of the present disclosure.

Turning to FIG. 2, a simplified block diagram of the medical system 10 is illustrated in accordance with an embodiment. The sensor 12 may include optical components in the form of the emitter 16 and the detector 18. The emitter 16 and the detector 18 may be arranged in a reflectance or transmission-type configuration with respect to one another. The emitter 16 may be a light emitting diode, superluminescent light emitting diode, a laser diode, or a vertical cavity surface emitting laser (VCSEL). The emitter 16 and the detector 18 may also include optical fiber sensing elements. Also, the emitter 16 may include two light emitting diodes (LEDs) that are configured to emit at least two wavelengths of light, e.g., red or near infrared light. In one embodiment, the LEDs emit light in the range of 600 nm to about 1000 nm. In a particular embodiment, the one LED is configured to emit light at 730 nm and the other LED is configured to emit light at 810 nm. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present disclosure. A time processing unit (TPU) may provide timing control signals to light drive circuitry, which may be configured to control and/or to adjust the light emitted by the emitter 16. For example, the light drive circuitry may control and/or adjust when the emitter 16 is activated. The TPU and/or the light drive circuitry may be provided within the monitor 14 or the sensor 12.

In one embodiment, light enters the detector 18 after passing through the tissue of the patient. In another embodiment, light emitted from the emitter 16 may be reflected by elements in the patent's tissue to enter the detector 18. The detector 18 may convert the received light at a given intensity, which may be directly related to the absorbance and/or reflectance of light in the tissue of the patient, into an electrical signal. After converting the received light to an electrical signal, the detector 18 may send the signal to the monitor 14, where signal characteristics may be analyzed and/or physiological characteristics may be calculated based at least in part on the absorption and/or reflection of light by the tissue of the patient.

As shown, the monitor 14 may include one or more processors 50, a memory 48, the display 20, and the speaker 21. The received signal may undergo synchronized demodulation, amplification, and/or filtering. In some embodiments, the processor 50 may be configured to receive user input via the input components 22. For example, in some cases, an operator may provide an input indicating the beginning and/or end of the administration of the CPR to the patient (e.g., causing the monitor 14 to initiate or to enter a "CPR mode" in which the non-cardiac pulses are identified and analyzed and/or in which information pertinent to CPR is displayed). In some embodiments, based at least in part upon the received signals corresponding to the light received by detector 18, the processor 50 may calculate the patient's $SpO_2$ using various algorithms. In some embodiments, the processor 50 may analyze characteristics of the signal (e.g., amplitude of non-cardiac pulses) and relate them to components of the CPR presently being administered to the patient using various algorithms. As discussed in more detail below, in some embodiments, the processor 50 may analyze the signal to identify whether the patient has experienced a ROSC.

To facilitate accurate monitoring of signal characteristics (e.g., amplitude of the non-cardiac pulses) and/or $SpO_2$ during CPR, the processor 50 may be configured to apply a pulse identification or qualification algorithm to identify and/or qualify modulations in the signal due to CPR (e.g., non-cardiac pulses due at least in part to chest compressions applied during CPR), and to thereby distinguish such non-cardiac pulses due to CPR from various signal artifacts (e.g., noise due to motion, ambient light, or the like). Such non-cardiac pulses may be qualified based on any of a variety of metrics (e.g., parameters), such as one or more pulse shape metrics (e.g., an amplitude, an amplitude variability, a center of area, a rotational moment, a mean, a median, a standard deviation, kurtosis, a pulse wave area, rise time, fall time, a mean path ratio, presence or absence of a dicrotic notch, a natural frequency, a period, a period variability, a damping factor, a skew, a derivative skew, or any combination thereof). As discussed in more detail below, non-cardiac pulses due to CPR may have a generally symmetric shape, a square shape, a sharp rise time, a sharp fall time, and/or lack a dicrotic notch. Thus, in some embodiments, it may be particularly useful to qualify non-cardiac pulses based on the rise time, fall time, and/or absence of the dicrotic notch. By way of another example, skew generally measures the asymmetry of a pulse around a mean or average value, and thus generally characterizes the degree of asymmetry and the shape of the pulse. Accordingly, in some embodiments, it may be useful to qualify the generally symmetric non-cardiac pulses due to CPR based on a skew metric. By way of another example, when CPR is assisted by an automated device, the non-cardiac CPR pulses may also have a certain amplitude, a certain period, and/or low variability in amplitude and/or period from pulse to pulse, and thus, such metrics may also be useful for qualifying non-cardiac pulses due to CPR. The metrics may be indicative of a feature of the pulse and may be compared with pulse qualification criteria (e.g., ranges or thresholds) to qualify or to disqualify the pulse as a non-cardiac pulse due to CPR. A pulse that satisfies the pulse qualification criteria is qualified as a non-cardiac pulse due to CPR, and a pulse that fails to satisfy the pulse qualification criteria is disqualified as a non-cardiac pulse due to CPR.

Additionally, in some embodiments, the pulse shape metrics utilized (e.g., by the processor 50) to qualify or to disqualify the pulses as non-cardiac pulses may be adjusted or selected (e.g., by the processor 50) based on whether the CPR is being performed or assisted by an automated CPR device or being performed manually by a person. Additionally or alternatively, in some embodiments, the pulse qualification criteria may be adjusted or selected (e.g., by the processor 50 based on user input) based on whether the CPR is being performed or assisted by an automated CPR device or being performed manually by a person. For example, when CPR is being performed or assisted by an automated CPR device, certain morphological features (e.g., an amplitude, an amplitude variability, a period, a period variability, a frequency, a rise time, a skew, or the like) may be particularly useful in qualifying non-cardiac pulses. Additionally, when CPR is being performed or assisted by an automated CPR device, the shape of non-cardiac pulses due to the CPR may be expected to have a specific shape and/or characteristics and may be qualified or disqualified based on a first set of relatively strict qualification criteria (e.g., limited ranges and/or lower thresholds for amplitude variability, pulse variability, skew, or the like). However, when CPR is being performed manually, certain and/or different morphological features (e.g., an amplitude, a period, a rise time, or the like) may be particularly useful in qualifying non-cardiac pulses. Additionally, when CPR is being performed manually, the shape, the amplitude, and/or period of the non-cardiac pulses due to CPR may be expected to have at least some inconsistencies and variation over time, and thus may be qualified or disqualified based on a second set of relatively relaxed qualification criteria (e.g., broad ranges and/or higher thresholds for amplitude, amplitude variability, or the like). The criteria (e.g., the first and second sets of criteria) may be stored within the memory 48, and the appropriate criteria may be accessed and utilized by the processor 50 based on whether the CPR is being performed or assisted by an automated CPR device or being performed manually by a person (e.g., as input via input 22). In some embodiments, the processor 50 may be configured to analyze the received signal and to determine whether the CPR is being performed or assisted by an automated CPR device or being performed manually by a person based on one or more metrics (e.g., pulse shape metrics), and the processor 50 may then qualify the non-cardiac pulses based on the appropriate criteria. As noted above, such qualification may differentiate the non-cardiac pulses due to CPR from noise (e.g., due to motion), thereby enabling accurate determination of the signal characteristics (e.g., amplitude of the non-cardiac pulses) and/or $SpO_2$ during CPR. In certain embodiments, the processor 50 may be configured to provide real-time feedback to adjust settings (e.g., rate, force, and/or depth of compressions) applied by an automated chest compression device communicatively coupled to the processor 50 based on the signal characteristics and/or $SpO_2$, for example.

Figure 3:
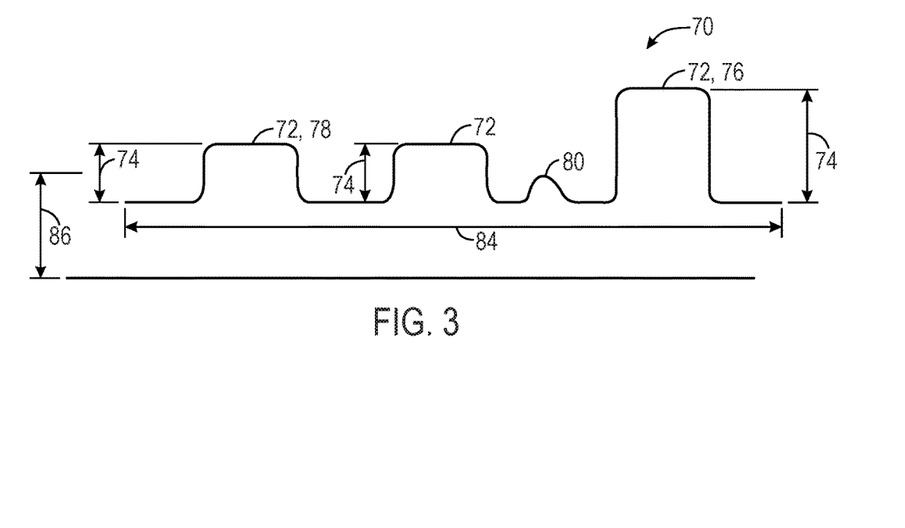
FIG. 3 is a graphical representation of a signal received from a sensor of the medical monitoring system of FIG. 1 during administration of CPR.

FIG. 3 provides an example of a signal 70 obtained from a sensor such as the sensor 12 during CPR. As shown, the signal 70 includes multiple non-cardiac pulses 72 due to CPR. Each non-cardiac pulse 72 includes a pulse amplitude 74 (i.e., peak to peak amplitude for the pulse 72). The pulse amplitude 74 may be related (e.g., linearly related) to the force applied during the chest compression and/or the effectiveness of the chest compression (e.g., location of the chest compression). For example, a stronger chest compression may result in a larger pulse amplitude 74 (see pulse amplitude 74 for relatively stronger pulse 76 in FIG. 3) relative to the pulse amplitude 74 from a weaker chest compression (see pulse amplitude 74 for relatively weaker pulse 78 in FIG. 3). Similarly, a chest compression administered in the wrong location (e.g., off-center) may result in a smaller pulse amplitude 74 (see pulse amplitude 74 for pulse 78 in FIG. 3) than a pulse amplitude 74 from a chest compression administered in the proper location (see pulse amplitude 76 for pulse 76 in FIG. 3). FIG. 3 also illustrates the pulse rate (i.e., frequency) of the signal 70 (i.e., the number of pulses 72 within a defined period of time 84). Generally the frequency of the detected pulses 72 may be the same as the frequency of the chest compressions administered during the CPR.

As shown, the non-cardiac pulses 72 due to CPR may have a generally symmetric shape, a square shape, a sharp rise time, a sharp fall time, a relatively low skew (e.g., as compared with regular cardiac pulses), lack a dicrotic notch, and/or have other distinguishing characteristics. The processor 50 may be configured to qualify the non-cardiac pulses 72 due to CPR and disqualify other modulations in the signal (e.g., modulation 80, which may be due to noise or the like) based on the metrics noted above. The processor 50 may also be configured to determine the patient's $SpO_2$ based on the qualified non-cardiac pulses. In some embodiments, the processor 50 may be configured to determine a resuscitation index (RI), which may be an indication of a percentage gain in the $SpO_2$ due to CPR over a time period. In certain embodiments, the processor 50 may be configured to determine the amplitude 74 of the non-cardiac pulses 72. In some embodiments, the amplitude 74 may be a normalized amplitude normalized by a baseline 86 of the signal 70. The processor 50 may compare the $SpO_2$ value and/or characteristics of the signal (e.g., the amplitude 74) to threshold values and/or ranges. For example, in some embodiments, the processor 50 may be configured to compare the amplitude 74 of the non-cardiac pulses 72 to an amplitude of pulses during spontaneous or normal circulation previously measured in the same patient or previously measured in similar patients (such as neonatal patients, or adult patients, or patients in a certain weight range). Such comparison, alone or in combination with the RI, may provide information related to a time period without circulation and a time period in which the patient experiences low circulation due to CPR. The processor 50 may be configured to communicate information related to the administered CPR (e.g., via the speaker 21 and/or display 20 as described above) based on these comparisons. For example, the processor 50, via the speaker 21 and/or display 20, may communicate to the person administering the CPR to adjust one or more components of the CPR (e.g., chest compressions and/or artificial respiration). The processor 50 may compare the $SpO_2$ value to a threshold value to determine if the $SpO_2$ value is lower than the threshold value and communicate to the person administering the CPR to adjust (e.g., increase) the frequency and/or intensity of breaths administered during the CPR if the $SpO_2$ value is lower than the threshold value.

An $SpO_2$ value below the threshold value may indicate that the patient 46 is not receiving enough oxygen. Alternatively, the processor 50 may be configured to determine if the $SpO_2$ value falls within an optimal range.

The processor 50 may also keep track of the number of compressions (e.g., via a number of qualified non-cardiac pulses 72) administered and communicate when artificial respiration should be administered. For example, the processor 50 may cause the monitor 14 to prompt the user (via audio or visual cues) to give a breath after a certain number, such as 20, compressions. The processor 50 may also compare the pulse amplitude 74 of the qualified non-cardiac pulses (e.g., the amplitude 74 of each non-cardiac pulse 72 and/or an average or a median amplitude 74 of multiple non-cardiac pulses 72 over a period of time) to an amplitude range (e.g., desired amplitude range) and communicate (e.g., via the speaker 21 and/or display 20 as described above) to the person administering the CPR to adjust chest compressions administered during the CPR if the amplitude 74 is not within the amplitude range. For example, if the amplitude 74 is below the desired amplitude range, the processor 50 may provide instructions to increase an intensity and/or a depth of chest compressions. If the amplitude 74 is above the desired amplitude range, the processor 50 may provide instructions to decrease the intensity and/or depth of chest compressions. In certain embodiments, the processor 50 may determine a change in the amplitude 74 across multiple non-cardiac pulses 72 over a period of time, which may be indicative of a consistency with which chest compressions are applied and/or whether the person applying CPR is tiring. For example, a change (e.g., an increase or a decrease) of less than approximately 5, 10, 15, or 20 percent amplitude 74 may be acceptable during manual CPR, while in some embodiments, a decrease of greater than approximately 10, 15, or 20 percent may indicate that the person applying CPR is tiring, in which case the processor 50 may provide appropriate feedback, such as suggesting that another person take over CPR if possible. In some embodiments, the processor 50 may also be configured to differentiate a downward trend in the amplitude 74 from a discrete, limited number of poor quality compressions, and provide the appropriate feedback, such as prompting the user to increase the depth or frequency of compressions. In some embodiments, the processor 50 may determine a number (e.g., percentage) indicative of the amplitude of the non-cardiac pulses relative to the target range or threshold, which may assist the person administering CPR in determining whether to adjust chest compressions. For example, the monitor 14 may display the percentage, so the user can see whether the compressions are approaching the correct amplitude. The amplitude range may be based on a nominal value determined through empirical data or inputted by a user. The amplitude range may be stored within the memory 48. In addition, the user may adjust and/or enter a desired amplitude range. Alternatively, the user may input patient characteristics (e.g., age, size, etc.), and/or information such as the patient's body tissue composition (e.g., obese) may be derived based on the signal obtained by the detector 18, and the processor 50 may be configured to adjust the amplitude range based on these patient characteristics. Alternatively, the processor 50 may receive an input and/or detect (e.g., via communication with the sensor 12) the type of sensor that is in use (e.g. adult, pediatric, infant) and adjust the amplitude range based on the patient population for the selected sensor. As noted above, one or more functions of the monitor 14 may also be implemented directly in the sensor 12.

Figure 4:
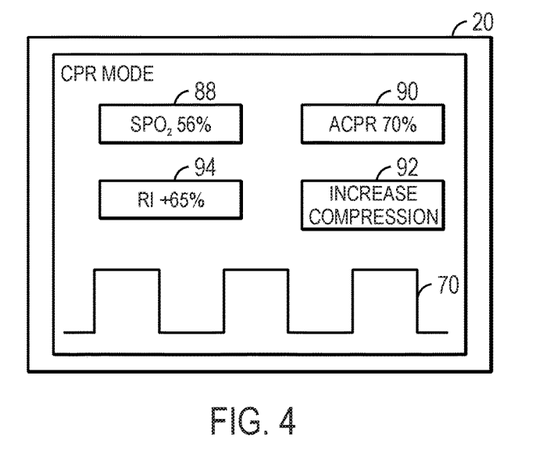
FIG. 4 is a front view of an embodiment of a display of the medical monitoring system of FIG. 1, in accordance with an aspect of the present disclosure.

FIG. 4 illustrates the monitor 14 and the display 20 during a CPR mode in which information pertinent to the administration of CPR is prominently displayed. By way of example, in operation, the operator may provide an input (e.g., via the input 22) indicating that CPR is beginning. Upon receipt of such input, the monitor 14 may enter the CPR mode and the processor 50 may cause the display 20 to remove, obscure, dim, block, or minimize certain information (e.g., irrelevant or less helpful information), such as the date, time, hemoglobin concentration, hematocrit levels, or other data that may be displayed by the monitor 14. Additionally, the processor 50 may cause the display 20 to highlight (e.g., via various colors or fonts) or expand certain information (e.g., relevant or more helpful information for CPR), such as the signal 70, the $SpO_2$ 88, the amplitude of the non-cardiac pulses (e.g., ACPR) or a number 90 (e.g., percentage) indicative of the amplitude of the non-cardiac pulses relative to the target range or threshold, instructions related to chest compressions or ventilation 92, or the like. As shown, the display 20 may provide the resuscitation index (RI) 94 indicative of a percentage gain in the $SpO_2$ due to CPR over a time period. For example, in the illustrated embodiment, the RI indicates that the $SpO_2$ has increased by approximately 65% since the beginning of administration of CPR and/or since entry into the CPR mode. In certain embodiments, the $SpO_2$ due to CPR may also be compared to the $SpO_2$ during normal perfusion, and an indication related to the CPR effectiveness (e.g., percentage of normal $SpO_2$ restored) may be provided on the display 20. In certain embodiments, data displayed on the display 20 while in the CPR mode may be defined and/or adjusted by the user (e.g., via input 22). In other embodiments, data displayed on the display 20 while in the CPR mode may be preset and stored in memory 48 of monitor 14 and automatically provided when CPR is initiated (e.g., as indicated based on user input and/or signal characteristics). As noted above, in some embodiments, data may be provided audibly via the speaker 21.

Figure 5:
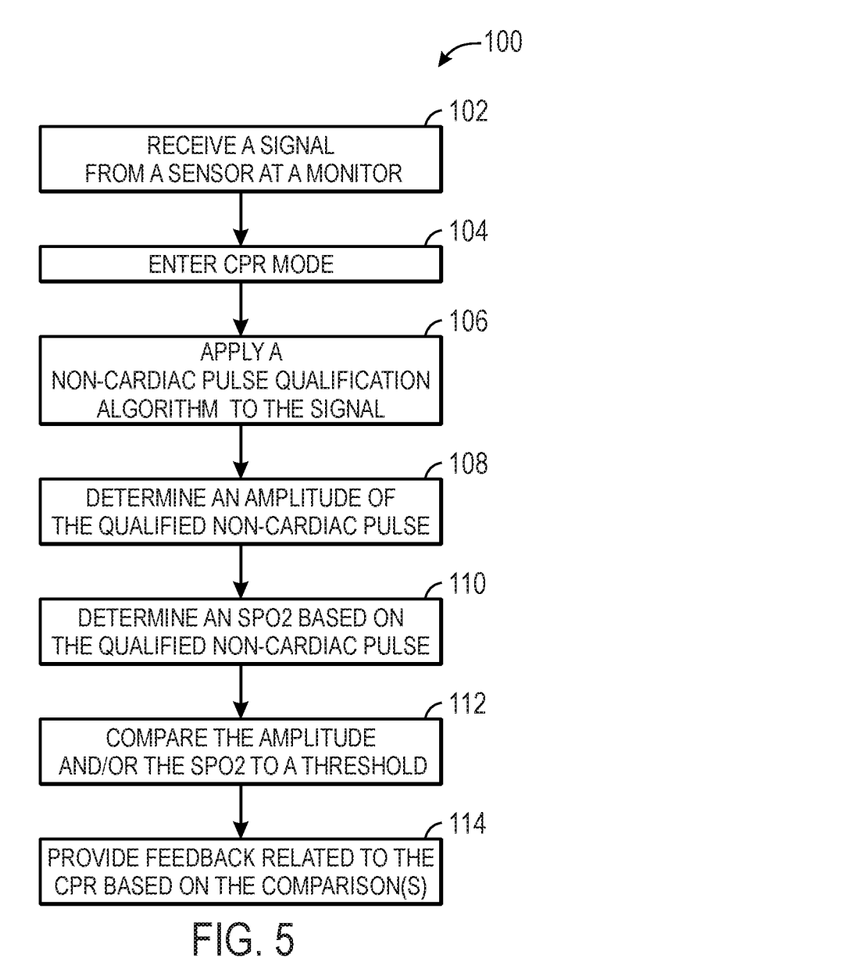
FIG. 5 is a process flow diagram of an embodiment of a method for using the medical monitoring system of FIG. 1.

As discussed above, the monitoring system 10 (e.g., the sensor 12 and/or the monitor 14) enable the analysis of physiological parameters (e.g., $SpO_2$ value) and/or signal characteristics (e.g., amplitude of non-cardiac pulses) to determine if the presently administered CPR needs to be adjusted, while also providing feedback with regard to one or more components of the CPR (e.g., chest compressions and/or artificial respiration). FIG. 5 generally illustrates a method 100 for utilizing the system 10 for this purpose. The methods disclosed herein include various steps represented by blocks. It should be noted any of the methods provided herein, may be performed as an automated procedure by a system, such as system 10. Although the flow charts illustrate the steps in a certain sequence, it should be understood that the steps may be performed in any suitable order and certain steps may be carried out simultaneously, where appropriate. Further, certain steps or portions of the methods may be performed by separate devices. For example, a first portion of the method may be performed by a blood pressure monitoring device, while a second portion of the method may be performed by the sensor 12 and/or monitor 14.

In step 102, the monitor 14 may receive the signal 70 from the sensor 12 applied to the patient. In step 104, the monitor 14 may enter into the CPR mode in which CPR feedback may be provided in accordance with the present disclosure. In certain embodiments, a user (e.g., a responder or the person administering the CPR) may provide an input (e.g., via input 22) that causes the monitor 14 to enter into the CPR mode (e.g., prior to administering CPR to the patient). In certain embodiments, the processor 50 may determine that CPR has begun based on signal characteristics and/or metrics (e.g., characteristics of the signal 70 received from the sensor 12), such as any of a variety of pulse shape metrics. In such cases, the monitor 14 may automatically enter the CPR mode upon administration of CPR (e.g., upon detection of qualified non-cardiac pulses in the signal 70). As noted above, non-cardiac pulses due to CPR may have certain characteristics or features that differ from typical cardiac pulses obtained during patient monitoring, and these characteristics may enable the processor 50 to determine that CPR has begun and may result in initiation of the CPR mode.

In step 106, the processor 50 may apply a pulse identification or qualification algorithm to identify and/or qualify modulations in the signal due to CPR (e.g., non-cardiac pulses), and thereby distinguish such non-cardiac pulses from various signal artifacts (e.g., noise due to motion, ambient light, or the like). Such non-cardiac pulses may be qualified based on any of a variety of metrics as described above. The metrics may be indicative of a feature of the pulse and may be compared with pulse qualification criteria (e.g., ranges or thresholds) to qualify or to disqualify the pulse. A pulse that satisfies the pulse qualification criteria is qualified as a non-cardiac pulse due to CPR, and a pulse that fails to satisfy the pulse qualification criteria is disqualified as a non-cardiac pulse due to CPR.

In step 108, the processor 50 may determine the amplitude of the qualified non-cardiac pulses due to CPR, as discussed above with respect to FIGS. 2 and 3. In certain embodiments, the processor 50 may determine the amplitude of each non-cardiac pulse and/or an average or a median amplitude of multiple non-cardiac pulses over a period of time. Additionally, in some cases, the amplitude may be a normalized amplitude normalized by a baseline of the signal. In step 110, the processor 50 may determine a physiological parameter (e.g., $SpO_2$) based on the qualified non-cardiac pulses. For example, the processor 50 may utilize various algorithms to determine the $SpO_2$ based at least in part upon the received signals corresponding to the light received by detector 18.

In step 112, the processor 50 may compare the amplitude of the non-cardiac pulses due to CPR and/or the $SpO_2$ to threshold values and/or ranges. The amplitude range and/or the $SpO_2$ range may be based on respective nominal values determined through empirical data or inputted by a user. The amplitude range and/or the $SpO_2$ range may be stored within the memory 48. In addition, the user may adjust and/or enter a desired amplitude range and/or $SpO_2$ range. Alternatively, the user may input patient characteristics (e.g., age, size, etc.), and the processor 50 may be configured to adjust the amplitude range and/or the $SpO_2$ range based on these patient characteristics. Alternatively, the processor 50 may receive an input and/or detect (e.g., via communication with the sensor 12) the type of sensor that is in use (e.g. adult, pediatric, infant) and adjust the amplitude range and/or the $SpO_2$ range based on the patient population for the selected sensor.

In step 114, the sensor 12 and/or the monitor 14 may provide feedback (e.g., via display 20 and/or speaker 21) to the provider based on the amplitude of the non-cardiac pulses due to CPR and the $SpO_2$ value (e.g., based on the comparison of the amplitude and/or the $SpO_2$ to a threshold or a range as discussed with respect to step 112). The feedback may confirm the proper administration of the CPR, provide an analysis of the CPR, and/or provide recommended adjustments for the administration of the CPR. For example, the processor 50, via the speaker 21 and/or display 20, may communicate to the person administering the CPR to adjust one or more components of the CPR (e.g., chest compressions and/or artificial respiration), as discussed above.

The patient may experience a return of spontaneous circulation (ROSC) during CPR. In general, once the patient experiences the ROSC, CPR should no longer be administered. Thus, in some embodiments, the sensor 12 and/or the monitor 14 may be configured to determine whether the ROSC has occurred and/or to provide feedback to the person administering CPR based on whether ROSC has occurred (e.g., instruct the person administering CPR to cease CPR if ROSC has occurred). In some embodiments, the occurrence of ROSC may be determined by analyzing the signal received from the sensor 12 with respect to any of a variety of signal metrics (e.g., parameters), or certain changes in such metrics, such as one or more pulse shape metrics. For example, in certain embodiments, the occurrence of the ROSC may be determined based on an amplitude or changes in amplitude of received pulses. Additionally or alternatively, the occurrence of the ROSC may be determined based on a correlation, or a lack of a correlation, between a time of application of chest compressions applied during CPR and pulses in the signal received from the sensor 12.

Figure 6:
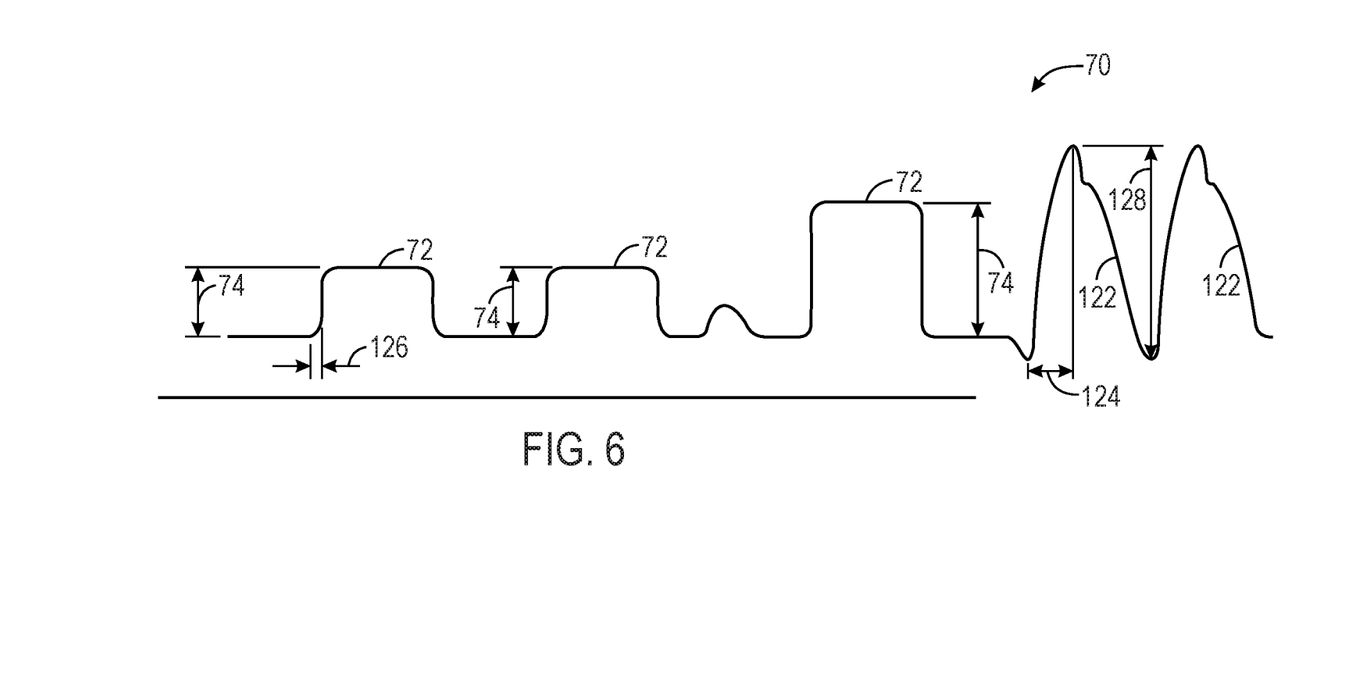
FIG. 6 is a graphical representation of a signal received from a sensor of the medical monitoring system of FIG. 1 showing non-cardiac pulses due to the administration of CPR and pulses due to a return of spontaneous circulation (ROSC)

With the foregoing in mind, FIG. 6 is a graphical representation of a signal 120 received from the sensor 12 during administration of CPR. The depicted signal 120 includes an example of non-cardiac pulses 72 due to CPR and ROSC pulses 122 (e.g., cardiac pulses) due to the ROSC. The ROSC pulses 122 may have particular features and characteristics (e.g., morphological characteristics) that enable identification of the ROSC. For example, the sensor 12 and/or the monitor 14 may be configured to apply a ROSC pulse identification or qualification algorithm to identify and/or qualify modulations in the signal due to the ROSC, and thereby distinguish such ROSC pulses 122 due to the ROSC from the non-cardiac pulses 72 due to CPR and/or from various signal artifacts (e.g., noise due to motion, ambient light, or the like). Such ROSC pulses 122 may be qualified based on any of a variety of metrics (e.g., parameters), such as one or more pulse shape metrics (e.g., an amplitude, an amplitude variability, a center of area, a rotational moment, a mean, a median, a standard deviation, kurtosis, a pulse wave area, rise time, fall time, a mean path ratio, presence or absence of a dicrotic notch, a natural frequency, a period, a period variability, a damping factor, a skew, a derivative skew, or any combination thereof). The metrics may be indicative of a feature of the ROSC pulse 122 and may be compared with ROSC pulse qualification criteria (e.g., ranges or thresholds) to qualify or to disqualify the pulse as an ROSC pulse 122. A pulse that satisfies the ROSC pulse qualification criteria is qualified as an ROSC pulse, and a pulse that fails to satisfy the pulse qualification criteria is disqualified as an ROSC pulse.

As shown, the non-cardiac pulses 72 and the ROSC pulses 122 have different features and characteristics (e.g., morphological characteristics) as compared to one another. For example, a rise time 124 of the ROSC pulses 122 may be greater than a rise time 126 of the non-cardiac pulses 72 due to CPR. By way of another example, an amplitude 128 of the ROSC pulses 122 may be greater than the amplitude 74 of the non-cardiac pulses 72 due to CPR. Furthermore, in some embodiments, the non-cardiac pulses 72 due to CPR may have a generally symmetric shape, a square shape, a relatively small skew, and/or no dicrotic notch, while the ROSC pulses 122 may be generally asymmetric, lack a square shape, have a relatively greater skew as compared to the non-cardiac pulses 72 due to CPR, and/or include a dicrotic notch. In some embodiments, a variability of the amplitude 128 of the ROSC pulses 122 may be less than a variability of the amplitude 74 of the non-cardiac pulses 72 due to CPR and/or a variability of a period of the ROSC pulses 122 may be less than a variability of the period of the non-cardiac pulses 72 due to CPR, particularly when CPR is performed manually. As noted above, during CPR, the rescuer may not apply chest compressions consistently (e.g., as the rescuer tires), thus resulting in such variability in amplitude 74 and/or period. By way of another example, as shown, a baseline of the signal during ROSC may be different (e.g., lower) than a baseline of the signal during CPR, which may be due at least in part to incomplete release of the chest that commonly occurs during manual CPR. Thus, in some embodiments, the sensor 12 and/or the monitor 14 may be configured to compare one or more metrics of the non-cardiac pulses 72 to one or more metrics of suspected ROSC pulses to identify and/or to confirm the occurrence of ROSC. For example, if a pulse having certain characteristics of ROSC pulses 122 is identified by the processor 50, the sensor 12 and/or the monitor 14 may compare one or more metrics, such as rise time and/or amplitude, of the suspected ROSC pulses to the previously identified non-cardiac pulses 72 to confirm that the pulse characteristics (e.g., rise time and/or amplitude) have changed and/or to confirm and/or support the determination that the patient has indeed experienced the ROSC.

Figure 7:
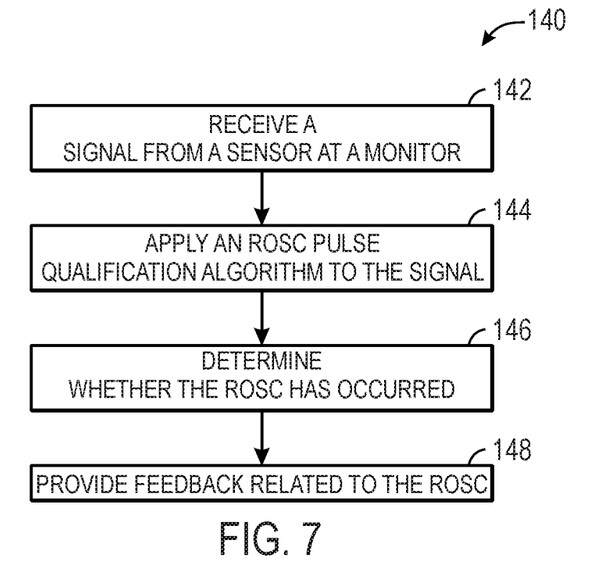
FIG. 7 is a process flow diagram of an embodiment of a method for using the medical monitoring system of FIG. 1 to identify the ROSC.

FIG. 7 generally illustrates a method 140 for utilizing the system 10 for identifying the ROSC. Some or all of the steps discussed with respect to FIG. 7 may be carried out in addition to some or all of the steps discussed with respect to FIG. 4 to facilitate the administration of CPR and to provide CPR feedback. In step 142, the monitor 14 may receive the signal 120 from the sensor 12 applied to the patient. In step 144, the processor 50 may apply an ROSC pulse identification or qualification algorithm and/or compare morphological features of the signal to ROSC pulse qualification criteria (e.g., ranges or thresholds) to identify and/or qualify modulations in the signal due to the ROSC (e.g., non-cardiac pulses), and thereby distinguish such ROSC pulses from non-cardiac pulses due to CPR and/or from various signal artifacts (e.g., noise due to motion, ambient light, or the like). Such ROSC pulses may be qualified based on any of a variety of metrics (e.g., parameters), such as one or more pulse shape metrics (e.g., an amplitude, a center of area, a rotational moment, a mean, a median, a standard deviation, kurtosis, a pulse wave area, rise time, fall time, a mean path ratio, presence, absence, depth, and/or timing of a dicrotic notch, a natural frequency, a damping factor, a skew, a derivative skew, or any combination thereof). The metrics may be indicative of a feature of the pulse and may be compared with ROSC pulse qualification criteria (e.g., ranges or thresholds) to qualify or to disqualify the pulse. A pulse that satisfies the pulse qualification criteria is qualified as an ROSC pulse, and a pulse that fails to satisfy the pulse qualification criteria is disqualified as an ROSC pulse.

In certain embodiments, the processor 50 may apply both the non-cardiac pulse identification or qualification algorithm to identify and/or qualify modulations in the signal due to CPR and the ROSC identification or qualification algorithm to identify and/or qualify modulations in the signal due to the ROSC (e.g., non-cardiac pulses) to each pulse. In other embodiments, the processor 50 may first apply the non-cardiac pulse identification or qualification algorithm to each pulse to qualify or to disqualify the pulse as a non-cardiac pulse. If the pulse is qualified as a non-cardiac pulse, the processor 50 may proceed to analyze the pulse as set forth above with respect to FIG. 5, for example. If the pulse is disqualified as a non-cardiac pulse, the processor 50 may then apply the ROSC identification or qualification algorithm to determine whether the pulse is due to the ROSC. In other embodiments, the processor 50 may first apply the ROSC pulse identification or qualification algorithm to each pulse to qualify or to disqualify the pulse as an ROSC pulse. If the pulse is qualified as an ROSC pulse, the processor 50 may proceed as set forth below. If the pulse is disqualified as an ROSC pulse, the processor 50 may then apply the non-cardiac pulse identification or qualification algorithm to determine whether the pulse is a non-cardiac pulse due to the CPR.

As noted above, if a pulse having certain characteristics of ROSC pulses is identified via the ROSC pulse identification or qualification algorithm, the sensor 12 and/or the monitor 14 may compare one or more metrics, such as rise time and/or amplitude, of the suspected ROSC pulse to one or more previously identified non-cardiac pulses 72. Such comparison may be used by the processor 50 to confirm that the pulse characteristics (e.g., rise time and/or amplitude) have changed and/or to confirm and/or support the determination that the patient has indeed experienced the ROSC.

In step 146, the processor 50 may determine whether the ROSC has occurred based on whether ROSC pulses are identified in step 144. In some embodiments, the processor 50 may determine that the patient has experienced the ROSC if one or more ROSC pulses are identified via step 144. In some embodiments, the processor 50 may determine that the patient has experienced the ROSC if at least a certain number of ROSC pulses are identified (e.g., more than 1, 2, 3, 4, 5, 6, 7, 8, 9, 10, or more) within a predetermined time period (e.g., 10, 15, 30, 45, 60 or more seconds).

In step 148, the sensor 12 and/or the monitor 14 may provide feedback (e.g., via display 20 and/or speaker 21) to the provider based on whether ROSC pulses are identified by step 144 and/or based on whether the ROSC has occurred as determined in step 146. In some embodiments, the feedback with respect to the ROSC may provide an indication of the occurrence or non-occurrence of ROSC pulses and/or the ROSC. In some embodiments, the feedback with respect to the ROSC may provide recommended adjustments for the administration of the CPR (e.g., a recommendation to cease CPR if the patient has experienced the ROSC or to pause CPR to better analyze the signals and/or the patient if the ROSC is probable, but not confirmed). By way of example, when one or more ROSC pulses are qualified via step 144, the processor 50, via the speaker 21 and/or display 20, may communicate to the person administering the CPR that the one or more ROSC pulses have been identified. Such feedback may provide an indication that the CPR has been effective and that the patient's normal cardiac function is returning. Additionally or alternatively, when the processor 50 determines that the ROSC has occurred at step 146 (e.g., based on one or more ROSC pulses identified in step 144), the processor 50, via the speaker 21 and/or display 20, may communicate to the person administering the CPR that the ROSC has occurred. In some embodiments, when the processor 50 determines that the ROSC has occurred at step 146 (e.g., based on one or more ROSC pulses identified in step 144), the processor 50, via the speaker 21 and/or display 20, may communicate to the person administering the CPR to stop delivery of CPR. In some embodiments, when the processor 50 determines that the ROSC has occurred at step 146 (e.g., based on one or more ROSC pulses identified in step 144), the processor 50 may cause the monitor 14 to exit the CPR mode, thereby ceasing display of information relevant to CPR and/or ceasing application of non-cardiac pulse qualification algorithms and/or ROSC qualification algorithms, for example.

In some embodiments, the processor 50 may continue to monitor the signal 120 for ROSC pulses. If subsequent pulses are qualified as ROSC pulses, the processor 50, via the speaker 21 and/or display 20, may provide confirmation that the patient's cardiac function has resumed. If a certain number of ROSC pulses occur over a predetermined period of time (e.g., 15, 30, 45, 60, or more seconds), the processor 50, via the speaker and/or display 20, may provide an indication that CPR monitoring is complete and/or the processor 50 may automatically exit the CPR mode. However, if one or more subsequent pulses fail to qualify as ROSC pulses and/or if a predetermined period of time (e.g., 5, 10, 15, 30, or more seconds) passes without a qualified ROSC pulse, then the processor 50, via the speaker 21 and/or display 20, may provide an alert or an indication to resume CPR. As noted above, one or more functions of the monitor 14 disclosed herein may also be implemented directly in the sensor 12.

Figure 8:
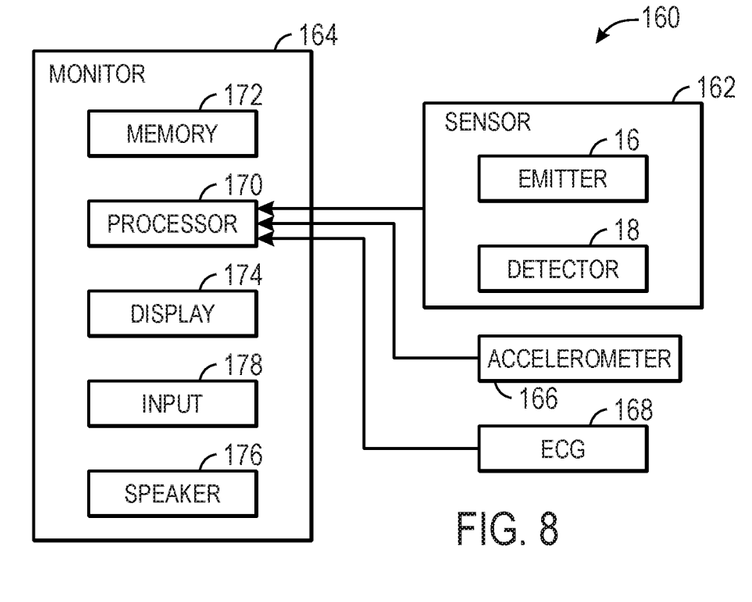
FIG. 8 is a block diagram of an embodiment of a medical monitoring system configured to monitor oxygen saturation and chest compressions during administration of CPR.

While the method discussed above with respect to FIG. 7 may monitor CPR and determine the ROSC via a single sensor 12, certain embodiments may include an additional sensor or device to monitor chest compressions to facilitate determination of whether the patient has experienced the ROSC. With the foregoing in mind, FIG. 8 is a simplified block diagram of a medical monitoring system 160 having a sensor 162 and a monitor 164. The system 160 may include an accelerometer 166 and/or an ECG sensor 168 to enable monitoring of chest compressions. The sensor 162 may be similar to or the same as the sensor 12 discussed above and may include optical components in the forms of the emitter 16 and the detector 18. The monitor 164 may be similar to and share at least some features with the monitor 14 discussed above. For example, the monitor 164 may include one or more processors 170, a memory 172, a display 174, a speaker 176, and/or an input 178 each of which may share any of the features and capabilities discussed above with respect to the monitor 14 and its components. For example, the monitor 164 may receive a signal from the sensor 162, and the processor 170 of the monitor 164 may calculate the $SpO_2$ using various algorithms, qualify non-cardiac pulses due to CPR, and/or analyze characteristics of the signal (e.g., amplitude of non-cardiac pulses), as discussed above. Additionally, the processor 170 may receive a signal from the accelerometer 166 and/or from the ECG sensor 168. As discussed in more detail below, the processor 170 may analyze the various signals received from the sensor 12, the accelerometer 166, and/or from the ECG sensor 168 to determine whether the patient has experienced the ROSC.

Generally, during CPR, each adequate chest compression causes (e.g., is correlated with or related to) a non-cardiac pulse 72 in the signal obtained by the sensor 12. However, after the ROSC, the signal obtained by the sensor 12 includes ROSC pulses 122 that may not be correlated with chest compressions. An input (e.g., a user input) and or a signal indicative of chest compressions applied during CPR may be compared with pulses in the signal obtained by the sensor 162 to determine whether the pulses are correlated with the chest compressions, and thus, whether the pulses are non-cardiac pulses due to CPR, for example, and/or whether the pulses are ROSC pulses due to the ROSC. In certain embodiments, the accelerometer 166 placed on or near the patient's chest may be utilized to monitor chest compressions and may provide the signal indicative of the chest compressions applied during CPR to the processor 170. Additionally or alternatively, the ECG sensor 168 may be utilized to track chest compressions and may provide the signal indicative of the chest compressions applied during CPR (e.g., the ECG signal may include portions affected by motion artifact from the chest compressions) to the processor 170.

As noted above, the processor 170 may receive the signal indicative of chest compressions from the accelerometer 166 and/or from the ECG sensor 168 and compare the signal indicative of chest compressions to the signal received from the sensor 12. If pulses obtained by the sensor 162 are not correlated with the chest compressions, the processor 50 may determine that the ROSC has occurred. However, if the pulses obtained by the sensor 12 are correlated with the chest compressions, the processor 50 may determine that ROSC has not occurred. It should be understood that the techniques for identifying the ROSC based on signals indicative of chest compressions (e.g., based on signals provided by the accelerometer 166 and/or by the ECG 168) may be utilized in conjunction with the techniques described with respect to FIGS. 1-7. For example, the processor 170 may determine that the ROSC has occurred based on the ROSC pulse identification and/or qualification algorithm, as discussed above with respect to FIG. 7, and based on whether the pulses are correlated with chest compressions. In such cases, the processor 170 may apply the ROSC pulse identification and/or qualification algorithm to pulses that are not correlated with chest compressions to confirm that the uncorrelated pulse is an ROSC pulse, for example.

Figure 9:
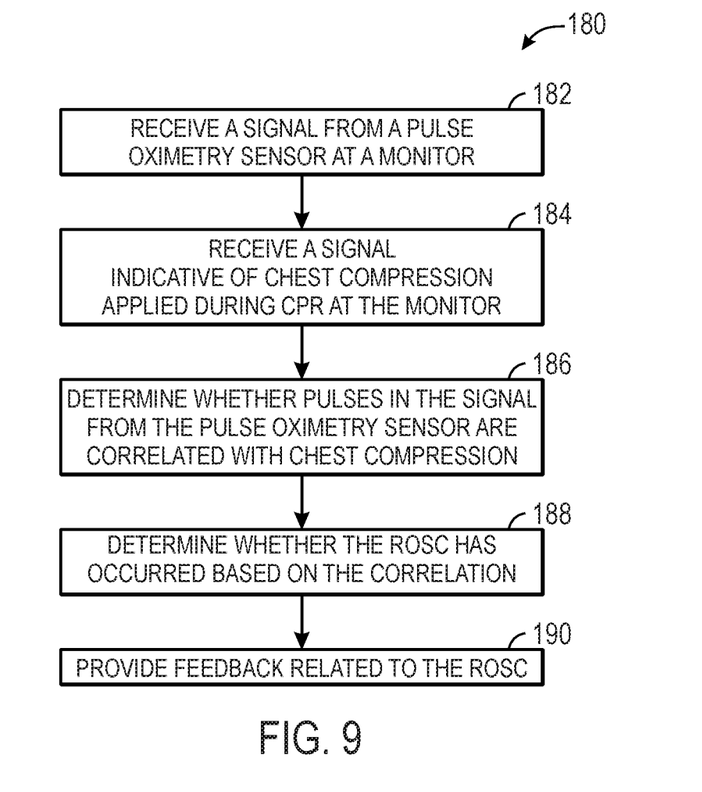
FIG. 9 is a process flow diagram of an embodiment of a method for using the medical monitoring system of FIG. 8 to identify the ROSC.

FIG. 9 generally illustrates a method 180 for utilizing the system 160 for identifying the ROSC. Some or all of the steps discussed with respect to FIG. 9 may be carried out in addition to some or all of the steps discussed with respect to FIG. 4 and/or FIG. 7 to facilitate the administration of CPR and to provide CPR feedback. In step 182, the monitor 170 may receive a signal from the sensor 162 applied to the patient. In step 184, the monitor 170 may receive an input (e.g., a user input) and/or a signal indicative of chest compressions applied to the patient during CPR. In certain embodiments, the signal indicative of chest compressions may be provided to the monitor 164 by the accelerometer 166 and/or by the ECG 168. In step 186, the processor 170 may determine whether pulses in the signal obtained by the sensor 162 correlate with the chest compressions.

In step 188, the processor 170 may determine whether the ROSC has occurred based at least in part on whether the pulses in the signal obtained by the sensor 12 correlate with the chest compressions. For example, if a pulse does not correlate with a chest compression, the processor 170 may determine that the pulse is an ROSC pulse. If a pulse does correlate with a chest compression, the processor 170 may determine that the pulse is a non-cardiac pulse and/or that the ROSC has not occurred. As discussed above with respect to FIG. 7, the processor 170 may determine that the ROSC has occurred if one or more ROSC pulses are identified and/or if multiple ROSC pulses are identified over a predetermined period of time. Additionally, the processor 170 may consider the correlation between the pulses and a time of application of the chest compressions in conjunction with other factors, such as whether the pulses are qualified as ROSC pulses based on application of the ROSC pulse identification and/or qualification algorithm. In step 190, the sensor 162 and/or the monitor 164 may provide feedback (e.g., via display 174 and/or speaker 176) to the provider based on whether the ROSC has occurred as determined in step 188. The feedback provided by the sensor 162 and/or the monitor 164 may be similar to that discussed above with respect to FIG. 7, for example.

In certain embodiments, the sensor 12, 162 may be configured to emit a single wavelength of light. While signals generated by such sensors 12, 162 may not enable calculation of $SpO_2$, the signals may enable the processor 50, 170 to monitor and/or to identify non-cardiac pulses due to CPR, the amplitude of such non-cardiac pulses, and/or the ROSC pulses. Thus, certain features of the disclosed techniques may be carried out with a simple, compact, and/or less costly sensor 12, 162.

In certain embodiments, the sensor 12, 162 may be adapted perform regional oximetry. In certain embodiments, an additional sensor configured to perform regional oximetry may be utilized in conjunction with the sensor 12, 162 to provide additional data regarding the efficacy and/or quality of the CPR. In regional oximetry, by comparing the relative intensities of light received at two or more detectors, it is possible to estimate the blood oxygen saturation of hemoglobin in a region of a body. For example, a regional oximeter may include a sensor to be placed on a patient's forehead and may be used to calculate the oxygen saturation of a patient's blood within the venous, arterial, and capillary systems of a region underlying the patient's forehead (e.g., in the cerebral cortex). In such cases, the sensor 12, 162 may include the emitter 16 and the two detectors 18: one detector that is relatively "close" to the emitter 16 and another detector that is relatively "far" from the emitter 16. Light intensity of one or more wavelengths may be received at both the "close" and the "far" detectors and. Thus, one detector may receive a first portion of light and the other detector may receive a second portion of light. Each of the detectors 18 may generate signals indicative of their respective portions of light. For example, the resulting signals may be contrasted to arrive at a regional saturation value that pertains to additional tissue through which the light received at the "far" detector passed (tissue in addition to the tissue through which the light received by the "close" detector passed, e.g., the brain tissue) when it was transmitted through a region of a patient (e.g., a patient's cranium). Surface data from the skin and skull is subtracted out to produce a regional oxygen saturation ($rSO_2$) value for deeper tissues.

In certain embodiments, the processor 50, 170 may be configured to determine an $rSO_2$ resuscitation index (RI), which may be an indication of a percentage gain in the $rSO_2$ due to CPR over a time period. In certain embodiments, the monitor 14, 164 may be configured to relate the $rSO_2$ value to the artificial respiration provided during the CPR. For example, the processor 50 may compare the $rSO_2$ value to threshold values and/or ranges. The processor 50 may be configured to communicate information related to the administered CPR (e.g., via the speaker 21 and/or display 20 as described above) based on these comparisons. For example, the processor 50, via the speaker 21 and/or display 20, may communicate to the person administering the CPR to adjust (e.g., increase) the frequency and/or intensity of breaths administered during the CPR if the $rSO_2$ value is lower than the threshold value. An $rSO_2$ value below the threshold value may indicate that the patient 46 is not receiving enough oxygen. Alternatively, the processor 50 may be configured to determine if the $rSO_2$ value falls within an optimal range. The $rSO_2$ or information indicative of the $rSO_2$ may be provided on the display 20 in a similar manner as discussed above with respect to the $SpO_2$ FIG. 4. Any of the techniques disclosed herein for monitoring the $SpO_2$ to determine CPR efficacy (e.g., receiving the signals, processing the signals, adjusting thresholds, determining and/or providing an appropriate output, or the like) may be adapted for monitoring the $rSO_2$ to determine CPR efficacy. Thus, in certain embodiments, the monitor 14, 164 may be configured to determine the rSO2, to determine the $SpO_2$, to identify the non-cardiac pulses, to analyze the amplitude of the non-cardiac pulses, and/or to identify the ROSC, for example. In some embodiments, the sensor 12, 162 and/or monitor 14, 164 may be configured to select the desired (e.g., strongest) signals from the signals provided by the two detectors 18 for use in determining the $rSO_2$ value, the $SpO_2$, and/or analyzing the signal characteristics related to one or more components of the CPR being administered in the manner discussed above. The sensor 12, 162 and/or monitor 14, 164 may be configured to provide feedback with respect to the CPR based on the $rSO_2$, the $SpO_2$, the amplitude of non-cardiac pulses, and/or the ROSC, as discussed above.

In some embodiments, a capnography device configured to monitor carbon dioxide content of exhaled breaths may provide an indication related to whether the patient is consuming oxygen and producing carbon dioxide. The capnography device may be used independently by the rescuer, or may be part of the system 10, 160 and provide a signal to the processor 50, 170, for example. The processor 50, 170 may receive and analyze the signal to determine whether CPR should cease or whether CPR should continue, and the processor 50, 170 may provide appropriate information via the display 20, 174. In some embodiments, the capnography device or another respiration sensor may provide an indication of whether the rescuer is providing too much or too little artificial respiration.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A medical monitoring system, comprising:
an oximetry sensor comprising a light emitter positioned to emit light into a patient and a photodetector positioned to generate a plethysmography signal; and
a monitor having a processor configured to:
receive the plethysmography signal from the oximetry sensor;
determine whether administration of cardiopulmonary resuscitation (CPR) is assisted by an automatic CPR device or is manually administered by a person based on the plethysmography signal;
select a first set of qualification criteria upon determining that the administration of CPR is via the automatic CPR device or a second set of qualification criteria upon determining that the administration of CPR is manually administered by the person;
identify within the plethysmography signal a non-cardiac pulse based on a first pulse shape metric and using the selected qualification criteria, the non-cardiac pulse being generated by the administration of CPR to the patient;
measure an oxygen saturation of the patient from the identified non-cardiac pulse; and
output the measured oxygen saturation to a visual display.

2. The system of claim 1, wherein the first pulse shape metric comprises an amplitude of the non-cardiac pulse.

3. The system of claim 2, wherein identifying the non-cardiac pulse comprises comparing the amplitude to a threshold amplitude of the non-cardiac pulse.

4. The system of claim 3, wherein the processor is further configured to provide feedback related to the administration of CPR, the feedback being based on a comparison between the amplitude of the non-cardiac pulse and the threshold amplitude of the non-cardiac pulse.

5. The system of claim 4, wherein the feedback comprises instructions to adjust a rate or a force of chest compressions applied to the patient during the administration of CPR.

6. The system of claim 1, wherein the first pulse shape metric comprises an amplitude variability, a center of area of the non-cardiac pulse, a rotational moment of the non-cardiac pulse, a mean, a median, a standard deviation, kurtosis, a pulse wave area, a rise time, a fall time, a mean path ratio of the non-cardiac pulse, presence or absence of a dicrotic notch, a natural frequency of the non-cardiac pulse, a damping factor of the non-cardiac pulse, a skew, or a derivative skew.

7. The system of claim 1, wherein the processor is configured to identify a return of spontaneous circulation (ROSC) based on a second pulse shape metric associated with a cardiac pulse.

8. The system of claim 7, wherein the second pulse shape metric comprises an amplitude, an amplitude variability, a center of area of the cardiac pulse, a rotational moment of the cardiac pulse, a mean, a median, a standard deviation, kurtosis, a pulse wave area, rise time, fall time, a mean path ratio of the cardiac pulse, presence or absence of a dicrotic notch, a natural frequency of the cardiac pulse, a period, a period variability, a damping factor of the cardiac pulse, a skew, or a derivative skew.

9. The system of claim 7, wherein the processor is configured to determine that the ROSC has occurred upon identification of multiple cardiac pulses within a period of time.

10. The system of claim 7, wherein the processor is configured to provide feedback to cease the administration of CPR when the ROSC has occurred.

11. The system of claim 1, wherein the processor is configured to receive an input indicative of a time of application of each chest compression applied during the administration of CPR, to compare the plethysmography signal to the input, and to classify a pulse of the plethysmography signal as indicative of a return to spontaneous circulation when the pulse does not correlate with the time of application of one of the chest compressions.

12. The system of claim 11, wherein the input comprises a signal obtained by an accelerometer positioned on a chest of the patient.

13. The system of claim 1, wherein the processor is configured to receive an input to initiate a CPR mode indicative of a beginning of the administration of CPR.

14. The system of claim 13, wherein the processor is configured to remove, obscure, dim, block, or minimize a portion of the visual display while in the CPR mode, wherein the portion of the visual display comprises information that is not associated with a CPR parameter.

15. The system of claim 13, wherein the processor is configured to highlight or expand a portion of the visual display while in the CPR mode, wherein the portion of the visual display comprises information associated with a CPR parameter.

16. The system of claim 15, wherein the information associated with the CPR parameter is the non-cardiac pulse, the oxygen saturation, an amplitude of the non-cardiac pulse, a number indicative of the amplitude of the non-cardiac pulse relative to a target range or an amplitude threshold of the non-cardiac pulse, instructions related to chest compressions, or instructions related to ventilation.

17. The system of claim 13, wherein the processor is configured to determine a resuscitation index (RI) indicative of a change in the oxygen saturation over time since initiation of the CPR mode.

18. The system of claim 17, wherein the RI is a percentage gain in the oxygen saturation.

\* \* \* \* \*